United States Patent
Clabeaux et al.

(10) Patent No.: US 11,452,865 B2
(45) Date of Patent: Sep. 27, 2022

(54) APPARATUS AND METHODS FOR MAKING COCHLEAR IMPLANT ELECTRODE ARRAYS

(71) Applicant: ADVANCED BIONICS AG, Staefa (CH)

(72) Inventors: Sarah Elizabeth Clabeaux, Ventura, CA (US); Mark Downing, Valencia, CA (US); Nicholas Wise, Pasadena, CA (US); Uli Gommel, Valencia, CA (US); Martin Sandoval-Perez, Canyon Country, CA (US); Morgan Gegg, Ventura, CA (US)

(73) Assignee: Advanced Bionics AG, Staefa (CH)

( * ) Notice: Subject to any disclaimer, the term of this patent is extended or adjusted under 35 U.S.C. 154(b) by 405 days.

(21) Appl. No.: 16/599,102

(22) Filed: Oct. 10, 2019

(65) Prior Publication Data
US 2021/0106816 A1   Apr. 15, 2021

(51) Int. Cl.
*A61N 1/05*   (2006.01)
*A61N 1/36*   (2006.01)
*A61F 11/20*   (2022.01)

(52) U.S. Cl.
CPC ....... *A61N 1/0541* (2013.01); *A61N 1/36038* (2017.08); *A61F 11/20* (2022.01)

(58) Field of Classification Search
CPC .... A61N 1/0541; A61N 1/36038; A61F 11/20
See application file for complete search history.

(56) References Cited

U.S. PATENT DOCUMENTS

| | | | |
|---|---|---|---|
| 4,686,765 | A | 8/1987 | Byers et al. |
| 5,000,194 | A | 3/1991 | Van Den Honert et al. |
| 5,037,497 | A | 8/1991 | Stypulkowski |
| 5,123,422 | A | 6/1992 | Charvin |
| 5,439,485 | A | 8/1995 | Mar et al. |
| 5,534,022 | A | 7/1996 | Hoffmann et al. |

(Continued)

FOREIGN PATENT DOCUMENTS

| | | |
|---|---|---|
| WO | WO2018/031025 A1 | 2/2018 |
| WO | WO2018/102695 A2 | 6/2018 |
| WO | WO 2018209872 A1 | 11/2018 |

OTHER PUBLICATIONS

U.S. Appl. No. 17/384,666, filed Jul. 23, 2021.
U.S. Appl. No. 17/232,131, filed Apr. 15, 2021.
U.S. Appl. No. 16/724,291, filed Dec. 21, 2019.

*Primary Examiner* — Lindsey G Wehrheim
(74) *Attorney, Agent, or Firm* — Henricks Slavin LLP (57) ABSTRACT

A method of forming an electrode array from an electrode array blank that includes a flexible body and a plurality of electrically conductive contacts. The method includes the steps of forming a first window in the flexible body that extends through the exterior of the flexible body to a first one of the electrically conductive contacts, the first window defining a first window perimetric center, and forming a second window in the flexible body that extends through the exterior of the flexible body to a second one of the electrically conductive contacts, the second window defining a second window perimetric center that is perimetrically offset from the first window perimetric center when the flexible body is straight and not twisted around the longitudinal axis of the flexible body.

22 Claims, 8 Drawing Sheets

(56) References Cited

U.S. PATENT DOCUMENTS

| | | |
|---|---|---|
| 5,542,173 A | 8/1996 | Mar et al. |
| 5,580,699 A | 12/1996 | Layman et al. |
| 5,658,709 A | 8/1997 | Layman et al. |
| 5,824,022 A | 10/1998 | Zilberman et al. |
| 6,125,302 A | 9/2000 | Kuzma |
| 6,144,883 A | 11/2000 | Kuzma |
| 6,195,586 B1 | 2/2001 | Kuzma |
| 6,309,410 B1 | 10/2001 | Kuzma et al. |
| 6,374,143 B1 | 4/2002 | Berrang et al. |
| 6,421,569 B1 | 7/2002 | Treaba et al. |
| 7,451,000 B2 | 11/2008 | Gibson et al. |
| 8,461,042 B2 | 6/2013 | Dadd et al. |
| 8,620,459 B2 | 12/2013 | Gibson et al. |
| 8,782,884 B2 | 7/2014 | Capcelea et al. |
| 9,694,174 B2 | 7/2017 | Dadd et al. |
| 10,406,350 B2 | 9/2019 | Mercanzini et al. |
| 11,103,703 B2 | 8/2021 | Krywcun et al. |
| 2003/0171787 A1 | 9/2003 | Money et al. |
| 2009/0306745 A1* | 12/2009 | Parker .......... A61N 1/0541 607/57 |
| 2010/0036470 A1 | 2/2010 | Nielsen |
| 2010/0287770 A1 | 11/2010 | Dadd et al. |
| 2011/0016710 A1 | 1/2011 | Dadd et al. |
| 2011/0126410 A1* | 6/2011 | Capcelea .......... B29C 45/0055 29/885 |
| 2013/0079749 A1 | 3/2013 | Overstreet et al. |
| 2013/0238074 A1 | 9/2013 | Zimmerling |
| 2014/0163662 A1 | 6/2014 | Beerling et al. |
| 2015/0032194 A1 | 1/2015 | Mergen et al. |
| 2015/0148736 A1* | 5/2015 | Jolly .......... A61M 31/002 604/20 |
| 2015/0246234 A1 | 9/2015 | Hazard et al. |
| 2016/0022990 A1 | 1/2016 | Risi |
| 2016/0082249 A1 | 3/2016 | Thenuwara et al. |
| 2016/0193460 A1 | 7/2016 | Xu et al. |
| 2017/0056646 A1 | 3/2017 | Sibary et al. |
| 2020/0188666 A1 | 6/2020 | Krywcun et al. |
| 2020/0384262 A1 | 12/2020 | Hoffman et al. |
| 2021/0187282 A1 | 6/2021 | Salvatierra |
| 2021/0236808 A1 | 8/2021 | Wise et al. |
| 2021/0346697 A1 | 11/2021 | Krywcun et al. |

* cited by examiner

APPARATUS AND METHODS FOR MAKING COCHLEAR IMPLANT ELECTRODE ARRAYS

BACKGROUND

1. Field

The present disclosure relates generally to the implantable portion of implantable cochlear stimulation (or "ICS") systems and, in particular, to electrode arrays.

2. Description of the Related Art

Figure 1:
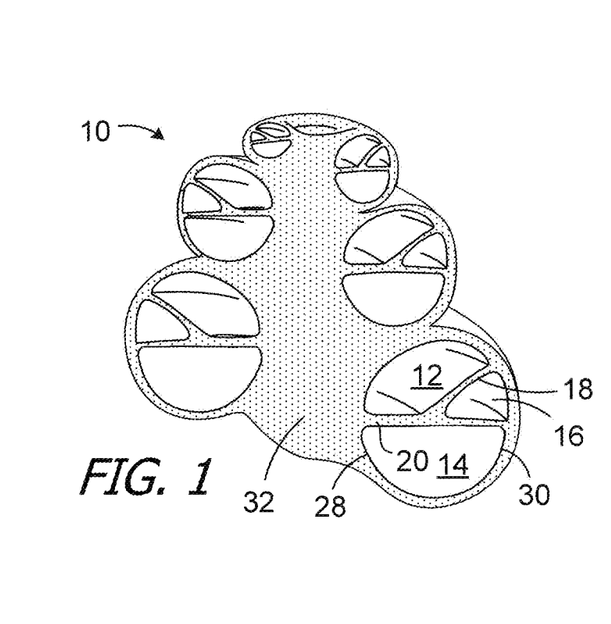
FIG. 1 is a section view of a cochlea.
Figure 2:
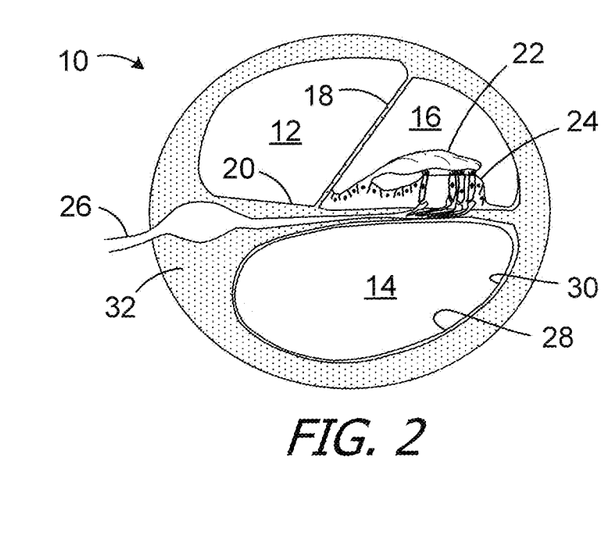
FIG. 2 is another section view of the cochlea.

Referring to FIGS. 1 and 2, the cochlea 10 is a hollow, helically coiled, tubular bone (similar to a nautilus shell) that is divided into the scala vestibuli 12, the scala tympani 14 and the scala media 16 by the Reissner's membrane 18 and the basilar membrane 20. The cochlea 10, which typically includes approximately two and a half helical turns, is filled with a fluid that moves in response to the vibrations coming from the middle ear. As the fluid moves, a tectorial membrane 22 and thousands of hair cells 24 are set in motion. The hair cells 24 convert that motion to electrical signals that are communicated via neurotransmitters to the auditory nerve 26, and transformed into electrical impulses known as action potentials, which are propagated to structures in the brainstem for further processing. Many profoundly deaf people have sensorineural hearing loss that can arise from the absence or the destruction of the hair cells 24 in the cochlea 10. Other aspects of the cochlea 10 illustrated in FIGS. 1 and 2 include the medial wall 28, the lateral wall 30 and the modiolus 32.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea of the inner ear, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material and a plurality of electrically conductive contacts (e.g., sixteen platinum contacts) spaced along a surface of the flexible body. The contacts of the array are connected to lead wires that extend through the flexible body. Exemplary cochlear leads are illustrated in WO2018/031025A1 and WO2018/102695A1.

The present inventors have determined that conventional cochlear implant electrode arrays, as well as conventional methods of making such arrays, are susceptible to improvement. For example, it is typically intended that after the electrode array is implanted within the cochlea, the contacts will all face the modiolus in the cochlea, which is where the spiral ganglion cells that innervate the hair cells are located. The present inventors have determined, however, that cochlear anatomy can cause the electrode array to twist as it is inserted deeper into the cochlea. The degree and location of twisting can vary from patient to patient and depends on each patient's anatomy and the length of the electrode array. The perception of sound may be adversely impacted in those instances where twisting of the electrode array results in some or all of the contacts not facing the modiolus. The efficiency of the cochlear implant system is also adversely effected, e.g., battery life is reduced, when the contacts are not facing the modiolus because higher current may be required (as compared to a properly oriented electrode array) for the patient to perceive a particular level of loudness.

SUMMARY

A method of forming an electrode array from an electrode array blank, which has a flexible body and a plurality of electrically conductive contacts, in accordance with one of the present inventions includes the steps of forming a first window in the flexible body that extends through the exterior of the flexible body to a first one of the electrically conductive contacts, the first window defining a first window perimetric center, and forming a second window in the flexible body that extends through the exterior of the flexible body to a second one of the electrically conductive contacts, the second window defining a second window perimetric center that is perimetrically offset from the first window perimetric center when the flexible body is straight and not twisted around the longitudinal axis of the flexible body.

A method in accordance with one of the present inventions includes the steps of inserting an electrode array into a cochlea having a modiolus, the electrode array including a flexible body, defining an exterior surface, a longitudinal axis and a perimeter that extends around the longitudinal axis in planes perpendicular to the longitudinal axis, a plurality of longitudinally spaced electrically conductive contacts that are below the exterior surface of the flexible body, and a plurality of longitudinally spaced windows that extend through the exterior of the flexible body to a respective electrically conductive contact and that define respective window perimetric centers, the window perimetric centers of at least some of the windows being perimetrically offset from the window perimetric centers of other windows when the flexible body is straight, and allowing at least a portion of the electrode array to twist a predetermined amount around the longitudinal axis during the insertion such that the window perimetric centers of all of the windows face modiolus when the electrode array is fully inserted into the cochlea.

A cochlear lead electrode array blank in accordance with one of the present inventions includes a flexible body formed from electrically non-conductive material and defining an outer surface, and a plurality of longitudinally spaced electrically conductive contacts that are entirely located inward of the outer surface of the flexible body and are completely covered by the flexible body.

There are a number of advantages associated with such methods and apparatus. By way of example, but not limitation, the present methods and apparatus may be used to form cochlear leads that are configured in such manner that the portions of the electrode array contacts exposed by the windows will face the modiolus within the cochlea after implantation despite twisting of the electrode array.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 3:
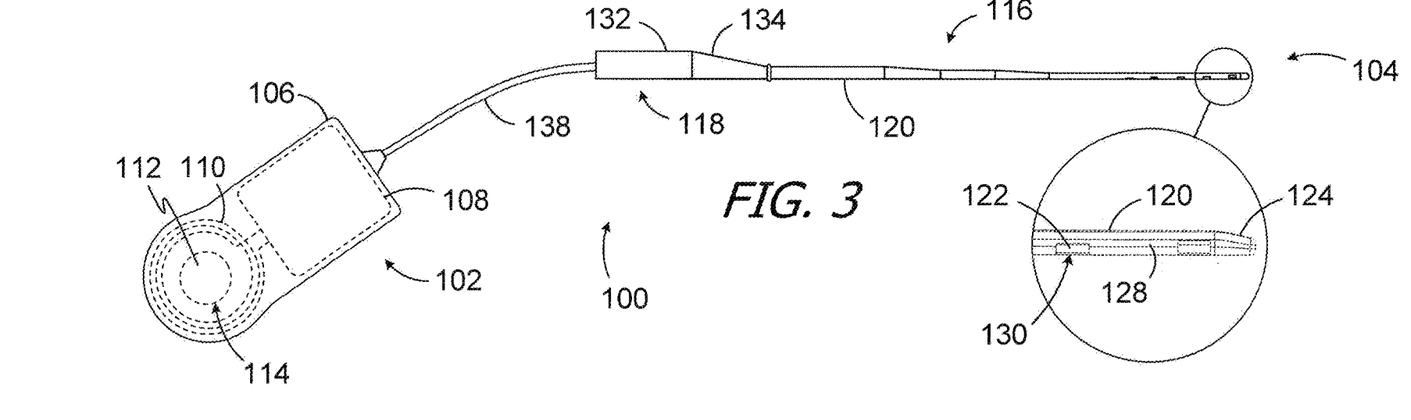
FIG. 3 is a plan view of a cochlear implant in accordance with one embodiment of a present invention.
Figure 4:
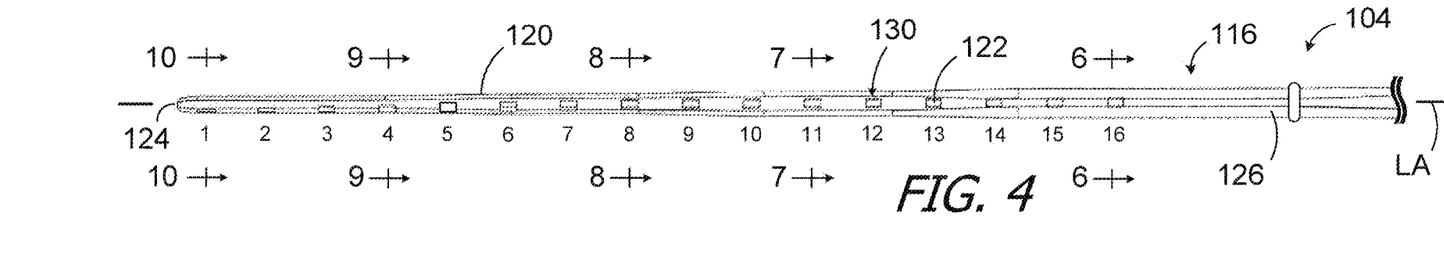
FIG. 4 is a bottom view of a cochlear lead electrode array in accordance with one embodiment of a present invention.
Figure 5:
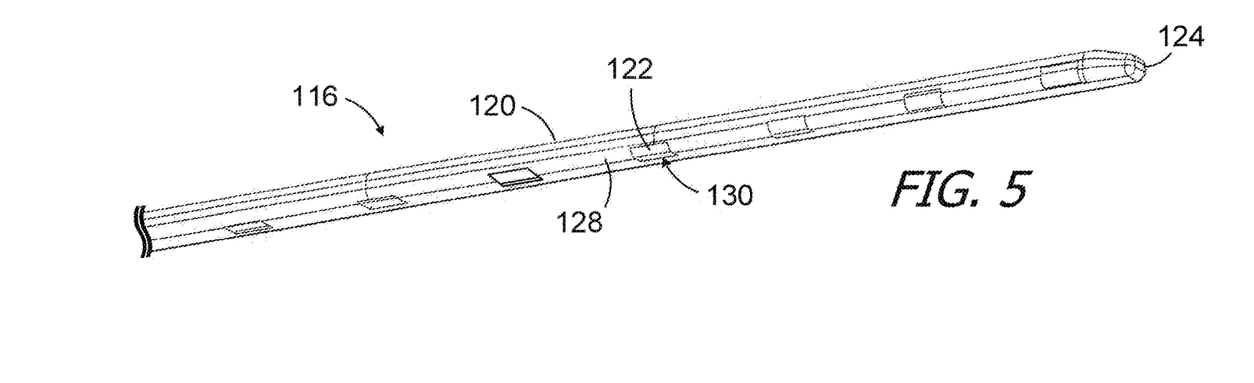
FIG. 5 is a perspective view of a portion of the cochlear lead electrode array illustrated in FIG. 4.

One example of a cochlear implant (or "implantable cochlear stimulator") in accordance with at least some of the present inventions is illustrated in FIGS. 3-10. Referring first to FIGS. 3-5, the exemplary cochlear implant 100 includes a stimulation assembly 102 and a cochlear lead 104.

A wide variety of stimulation assemblies may be combined with the present cochlear leads. The exemplary stimulation assembly 102 illustrated in FIG. 3 includes a flexible housing 106 formed from a silicone elastomer or other suitable material, a processor assembly 108, an antenna 110 that may be used to receive data and power by way of an external antenna that is associated with, for example, a sound processor unit, and a positioning magnet 112 located within a magnet pocket 114. The magnet 112 is used to maintain the position of a sound processor headpiece over the antenna 110. The cochlear implant may, in some instances, be configured is manner that facilitates magnet removal and replacement. Here, the housing 106 may be provided with a magnet aperture (not shown) that extends from the magnet pocket 114 to the exterior of the housing.

The exemplary cochlear lead 104 illustrated in FIGS. 3-5 includes an electrode array 116 and, in at least some instances, a wing 118 that functions as a handle for the surgeon during the implantation surgery. The exemplary electrode array 116 has a flexible body 120 and a plurality of electrically conductive contacts 122 (e.g., the sixteen contacts 122 illustrated in FIG. 4) spaced along the flexible body between the tip (or "apical") end 124 and the base (or "basal") end 126. The electrically conductive contacts 122 (or "contacts") may be located inward of the flexibly body outer surface 128 and exposed by way of a corresponding plurality of contact windows (or "windows") 130 that extend through the outer surface of the flexible body to the contacts. As is discussed in greater detail with references to FIGS. 6-10, one or more of the windows 130 may be perimetrically offset from other windows when the electrode array 116 is in a state where the electrode array 116 is straight and is not twisted around its longitudinal axis LA (see FIGS. 3 and 4) by torsional forces. The perimetric offsets may be used to account for twisting of the electrode array 116 that occurs during insertion. If, for example, a contact 122 is on a portion of the flexible body 120 that is expected to twist 50° around the longitudinal axis during the insertion, then the associated window 130 may be perimetrically offset by 50° in the opposite direction from what would have been its untwisted location. This allows the present cochlear leads 104 to be configured, e.g., based in part on patient-specific information or averages associated with known insertion data, in such manner that the portions of the electrode array contacts 122 exposed by the windows 130 will face the modiolus within the cochlea after implantation despite twisting of the electrode array around the longitudinal axis LA. As a result, the present cochlear leads will not adversely impact the patient's perception of sound or the efficiency of the associated cochlear implant system, as can be the case with cochlear leads having contacts that do not face the modiolus when the electrode array twists during insertion.

The wing 118 of the exemplary cochlear lead 104 illustrated in FIGS. 3-5 may include a rectangular portion 132 and a tapered portion 134 and, in addition to functioning as a handle, the wing provides tension relief for lead wires 136 (FIGS. 5A and 6) that do not run straight through the wing. A tubular member 138, which may consist of tubes of different sizes, extends from the wing 118 to the stimulation assembly housing 106. The contacts 122 are connected to the lead wires 136, and the lead wires extend through the flexible body 120 and tubular member 138 to a connector (not shown) in the housing 106. The connection between the stimulation assembly 102 and a cochlear lead 104 may be a temporary connection, whereby the stimulation assembly and a cochlear lead may be disconnected from one another (e.g., for in situ replacement of the stimulation assembly), or a permanent connection.

Although the present inventions are not so limited, the flexible body 120 of the exemplary electrode array 116 has a non-circular shape with a flat bottom (note FIGS. 6-10) in a cross-section perpendicular to the longitudinal axis LA. The flexible body 120 may also be tapered, with a perimeter in a plane perpendicular to the longitudinal axis LA that is smaller at the tip end 124 than at the base end 126. The shape of the flexible body 120 also varies along the length of the flexible body. Any other suitable flexible body shapes (e.g., circular or oval), with or without a flat surface, may also be employed. Suitable materials for the flexible body 120 include, but are not limited to, electrically non-conductive resilient materials such as LSR, high temperature vulcanization ("HTV") silicone rubbers, room temperature vulcanization ("RTV") silicone rubbers, and thermoplastic elastomers ("TPEs").

Figure 5A:
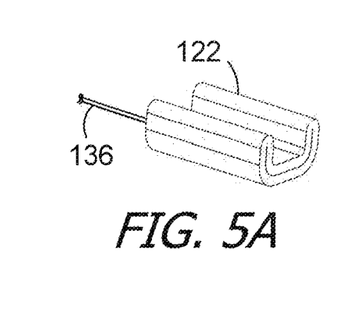
FIG. 5A is a perspective view of a portion of the cochlear lead electrode array illustrated in FIG. 4.

As illustrated for example in FIG. 4, the exemplary contacts 122 may be referred to in numbered order, 1st through 16th in the sixteen contact illustrated implementation, with the contact closest to the tip end 124 being the 1st contact and the contact closest to the base end 126 being the 16th contact. The contacts 122 are also the same size and shape in the illustrated implementation. Suitable materials for the contacts 122 include, but are not limited to, platinum, platinum-iridium, gold and palladium. Referring to FIG. 5A, the exemplary contacts 122 may be generally U-shaped and may be formed by a placing a tubular workpiece into an appropriately shaped fixture, placing the end of a lead wire into the workpiece, and then applying heat and pressure to the workpiece to compress the workpiece onto the lead wire. The insulation may be removed from the portion of the lead wire within the workpiece prior to the application of heat and pressure or during the application of heat and pressure. Various examples of tubular workpieces being compressed onto lead wires are described in WO2018/031025A1 and WO2018/102695A1, which are incorporated herein by reference.

Figure 5B:
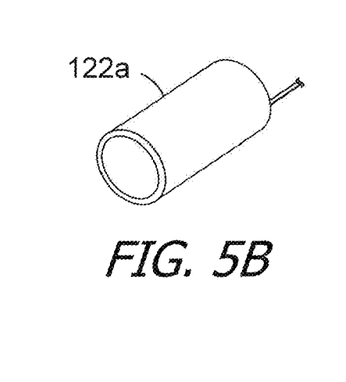
FIG. 5B is a perspective view of a portion of a cochlear lead electrode array in accordance with one embodiment of a present invention.

In other implementations, the contacts in an electrode array may be different in size and/or shape. For example, the contacts may be larger in the basal region than in the apical region. The contacts may be rings 122a (FIG. 5B) that extend completely around the longitudinal axis LA in the apical region, or contacts that only extend about half-way around the longitudinal axis LA in the basal region. Alternatively, or in addition, the length (in the direction of the longitudinal axis LA) of the contacts in an electrode array may be the same or different.

As noted above, one or more of the windows 130 may be perimetrically offset from other windows of the electrode array 116, which facilitates accurate orientation of the windows 130 relative to the modiolus when the electrode array 116 (or portions thereof) is in a twisted state after the insertion into the cochlea. To facilitate this discussion, the contacts and windows are referred to generically herein as "contacts 122" and "windows 130," while references to specific contacts and windows include the contact number and window number, e.g., "contact 122-16" and "window 130-16." Referring to FIG. 6, as used herein, the perimeter of the electrode array 116 (which is the perimeter of the flexible body 120) is defined by the outer surface of the flexible body 120 in a plane perpendicular to the longitudinal axis LA, and the perimetric direction follows the perimeter around the electrode array 116 (and flexible body 120) in that plane, as is shown by arrow PD. The perimetric center PC of each window 130 is the mid-point of the window in the perimetric direction.

The exemplary electrode array 116 is configured for a situation in which the surgeon expects that the basal portion of the electrode array will not be twisted when the insertion is complete, while apical portion of the electrode array will twist in a relatively consistent manner from one contact 122 to the next. Accordingly, as can be seen in FIG. 4, the basal eight (8) windows 130, i.e., windows 130-16 to 130-9, are aligned with one another in the perimetric direction, while the apical eight (8) windows, i.e., windows 130-8 to 130-1, are offset from the basal windows in the perimetric direction in respective increments that increase from one window to the next. Although the present inventions are not limited to any particular perimetric offset or offset pattern, the windows 130-8 to 130-1 are offset by the same amount from one parametric center PC to next. As a result, the respective portions of the contacts 122-8 to 122-1 that are exposed by way of the windows 130-8 to 130-1 are not the same. The respective portions of the contacts 122-8 to 122-1 that are exposed by way of the windows 130-8 to 130-1 are also different than the portions of contacts 122-16 to 122-9 that are exposed by way of the windows 130-16 to 130-9. By way of example, but not limitation, in other implementations, the perimetric offsets may begin in the more basal windows (e.g., window 130-13) or may begin in the more apical windows (e.g., window 130-4). The magnitude of the perimetric offsets may also vary. As is discussed in greater detail below with reference to FIG. 26, the parametric positions may be selected based on patient-specific information or averages associated with known insertion data.

Figure 6:
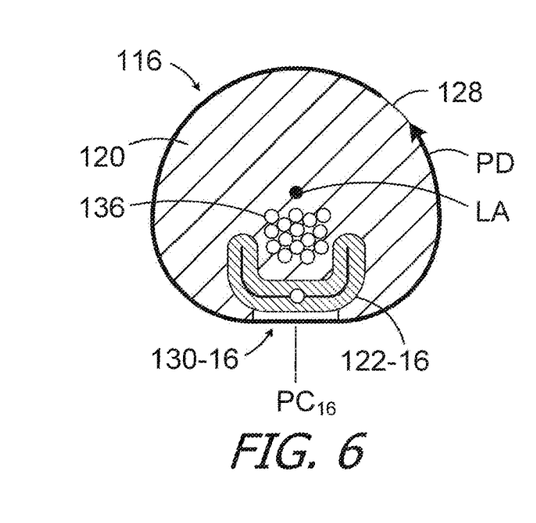
FIG. 6 is a section view taken along line 6-6 in FIG. 4.
Figure 7:
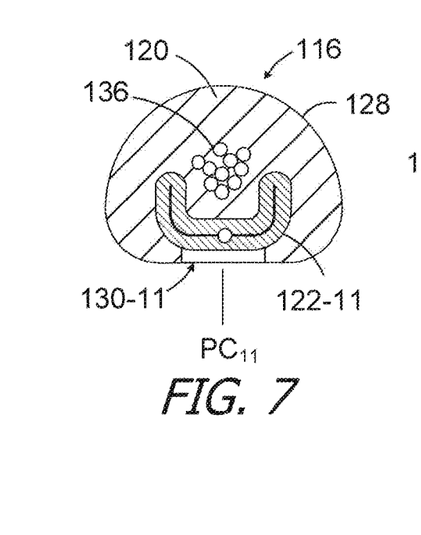
FIG. 7 is a section view taken along line 7-7 in FIG. 4.
Figure 8:
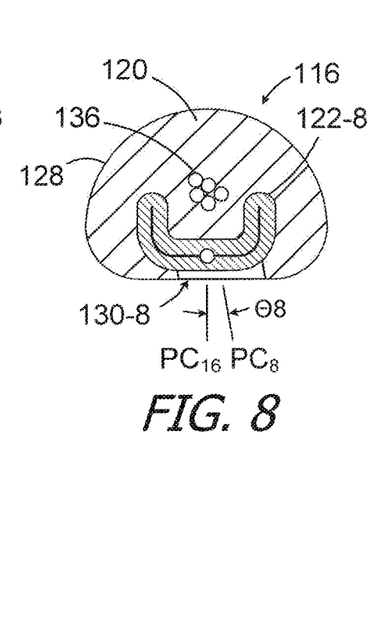
FIG. 8 is a section view taken along line 8-8 in FIG. 4.
Figure 9:
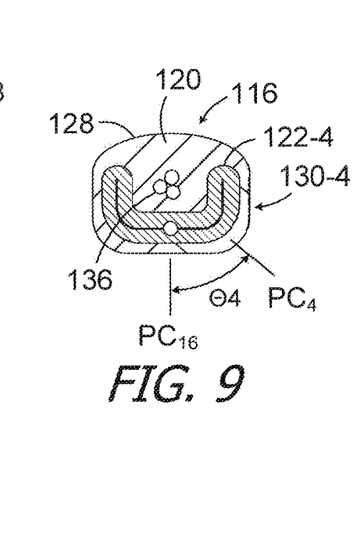
FIG. 9 is a section view taken along line 9-9 in FIG. 4.
Figure 10:
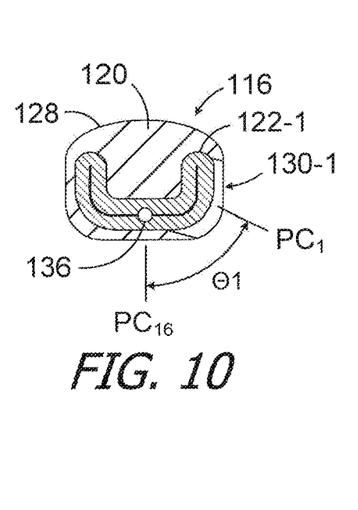
FIG. 10 is a section view taken along line 10-10 in FIG. 4.

The window and parametric center locations of the exemplary electrode array 116 in a non-twisted state are illustrated in FIGS. 6-10. Referring first to FIGS. 6 and 7, which are cross-sections taken through contacts 122-16 and 122-11, the associated windows 130-16 and 130-11 have perimetric centers $PC_{16}$ and $PC_{11}$ that are aligned with one another in the parametric direction PD. The perimetric center $PC_8$ of the window 130-8 associated with contact 122-8 (FIG. 8), on the other hand, is offset in the perimetric direction PD from the perimetric center $PC_{16}$ of the window 130-16 (as well as from the perimetric centers of windows 130-15 to 130-9) by angle Θ8. Although the present inventions are not so limited, angle Θ8 is about 10° in the illustrated implementation, and the angle of each successive perimetric offset is about 10° from the adjacent offset. As used herein in the context of angles, the word "about" means ±3-5°. The perimetric center $PC_4$ of the window 130-4 associated with contact 122-4 (FIG. 9) is offset in the perimetric direction from the perimetric center $PC_{16}$ of the window 130-16 (as well as from the perimetric centers of windows 130-15 to 130-9) by angle Θ4, which is equal to about 50° in the illustrated implementation. The perimetric center $PC_1$ of the window 130-1 associated with apical-most contact 122-1 (FIG. 10) is offset in the perimetric direction from the perimetric center $PC_{16}$ of the window 130-16 (as well as from the perimetric centers of windows 130-15 to 130-9) by angle Θ1, which is equal to about 80° in the illustrated implementation.

The contact windows 130 in the exemplary implementation are the same size and shape. However, in other implementations, the contact windows in an electrode array may be different in size in the longitudinal direction and/or in the perimetric direction and/or different in shape. For example, the windows may be larger in the basal region than in the apical region. Alternatively, or in addition, the spacing between the windows may also be varied. For example, in those instances where the length of the windows in the longitudinal direction is less than that of the contacts, the distance between the windows may be varied even when the distance between the contacts is the same.

Figure 11:
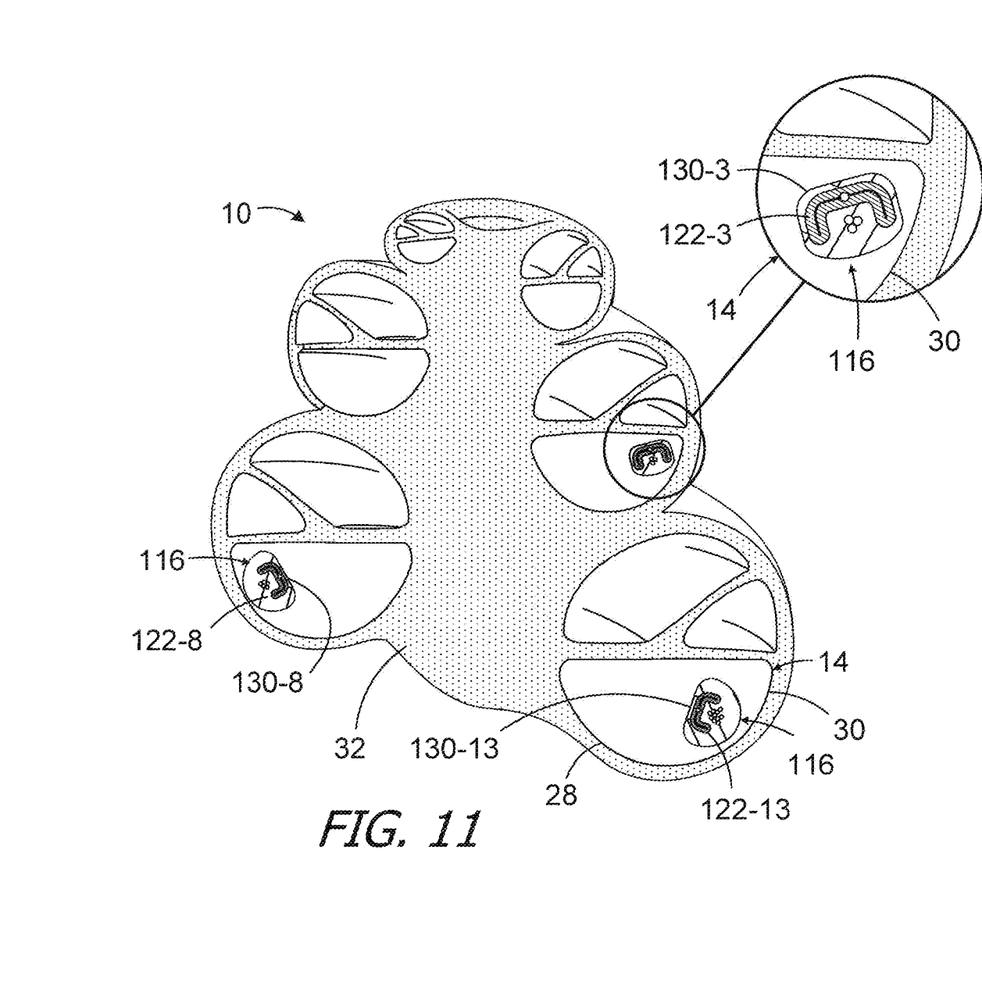
FIG. 11 is a section view of the cochlear electrode array illustrated in FIGS. 3-10 positioned within a cochlea.

Turning to FIG. 11, it can be seen that despite the twisting of the exemplary array 116 within the scala tympani 14, the windows 130 are facing the medial wall 28 and the modiolus 32. In particular, the portion of the electrode array 116 that include contacts 122-1 to 122-8 (and windows 130-1 to 130-8) has twisted, and contacts 122-3, 122-8 and 122-13 (and windows 130-3, 130-8 to 130-13) are visible is the illustrated section view. Despite the twisting of the apical portion of the electrode array 116, the windows 130-3 and 130-8 (and the exposed portions of contacts 122-3 and 122-8) are facing the medial wall 28 and the modiolus 32, as is the window 130-13 (and the exposed portion of contact 122-13) in the untwisted basal portion.

Figure 11A:
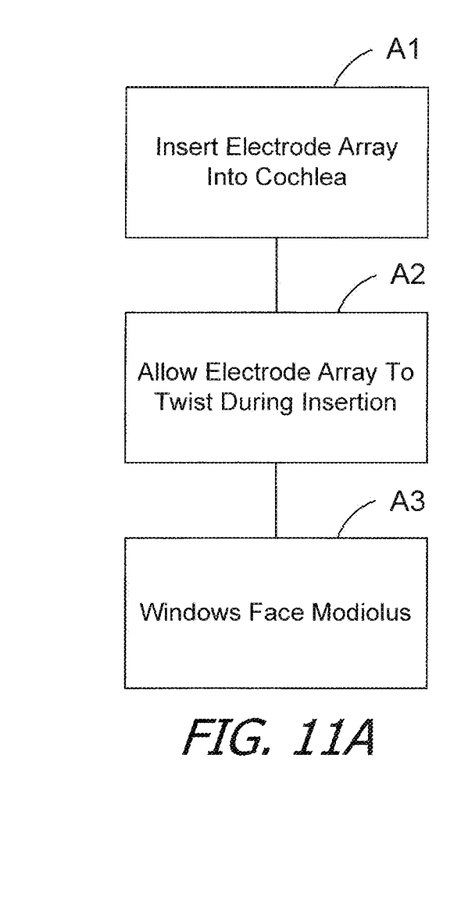
FIG. 11A is a flow chart showing a method in accordance with one embodiment of a present invention.

Put another way, and referring to FIG. 11A, the exemplary electrode array 116 may be inserted into the cochlea. [Step A1.] At least a portion of the electrode array is allowed to twist a predetermined (or "known" or "anticipated") amount around the longitudinal axis LA of the flexible body 120 of the electrode array 116. [Step A2.] The perimetric offset of the windows 130 in the portion of the electrode array 116 that is allowed to twist is such that, when the electrode array is fully inserted into the cochlea and has twisted the predetermined amount, the windows on both the twisted and non-twisted portions of the electrode array will face the modiolus. [Step A3.]

Figure 11B:
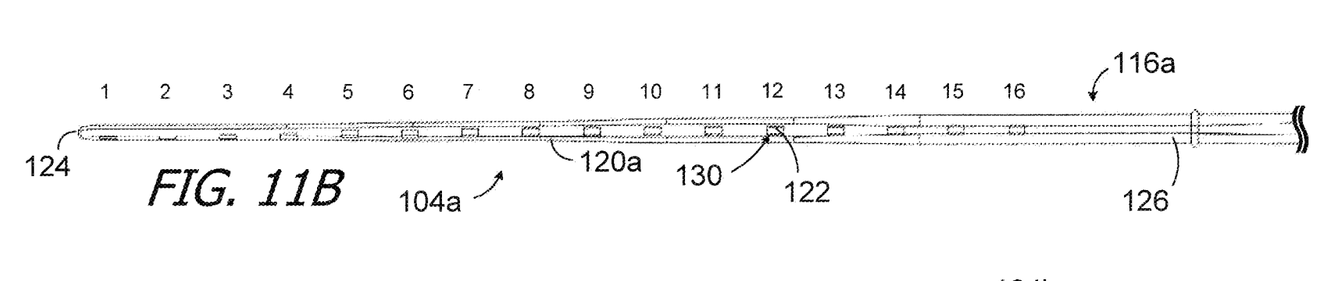
FIG. 11B is a bottom view of a cochlear lead electrode array in accordance with one embodiment of a present invention.
Figures 12, 13, 14, 15:
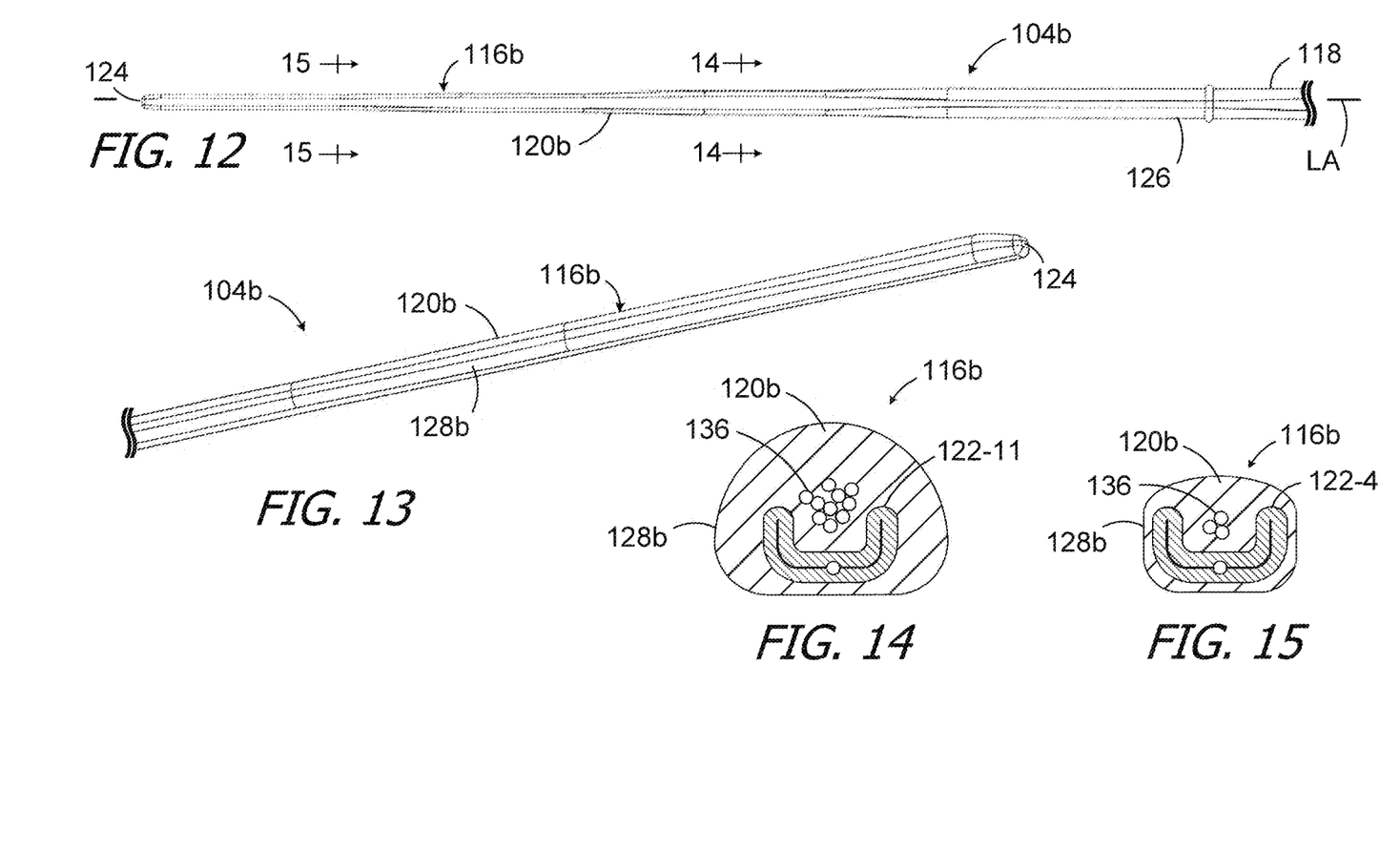
FIG. 12 is a bottom view of a cochlear lead blank in accordance with one embodiment of a present invention.
FIG. 13 is a perspective view of the cochlear lead blank illustrated in FIG. 12.
FIG. 14 is a section view taken along line 14-14 in FIG. 12.
FIG. 15 is a section view taken along line 15-15 in FIG. 12.
Figure 16:
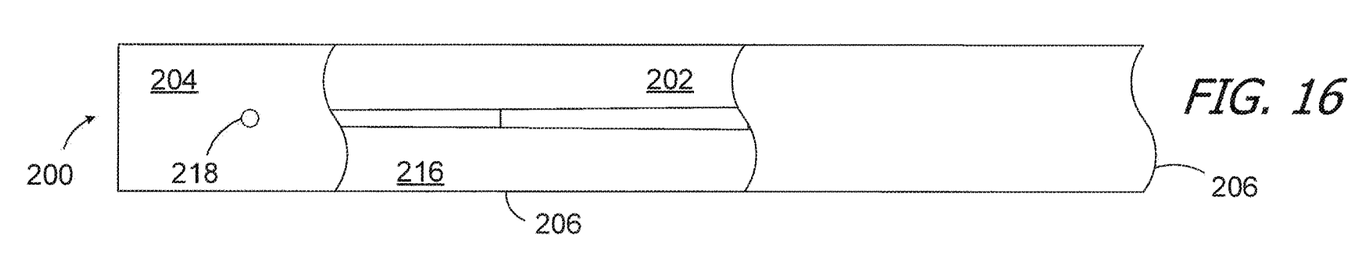
FIG. 16 is a top view of a mold in accordance with one embodiment of a present invention.

In other embodiments, the electrode array flexible body may be stiffer in the basal region in order to limit or prevent twisting of the basal region of the electrode array. Referring to FIG. 11B, the exemplary cochlear lead 104a illustrated therein is essentially identical to cochlear lead 104 and similar element are identified by similar reference numerals. To that end, the cochlear lead 104a includes an electrode array 116a with a flexible body 120a, a plurality of conductive contacts 122 and a corresponding plurality of windows 130. Here, however, a basal portion of the electrode array 116a (e.g., from the basal end 126 to contact 122-8) is stiffer that the remainder of the electrode array and, accordingly, resists twisting more that the same portion of the electrode array 116. The increased stiffness may be accomplished in any suitable manner. For example, in the illustrated implementation, the stiffer basal portion of the flexible body 120a is formed from stiffer material than the remainder of the flexible body. Alternatively, or in addition, contact sizes/ shapes that result in electrode arrays (or portions thereof) that are less likely to twist may be employed.

In accordance with another invention herein, cochlear leads having various differing window orientations and/or configurations may be formed from a common cochlear lead blank from which material is removed to form the windows. One example of such a cochlear lead blank is generally represented by reference numeral 104b in FIGS. 12-15. The exemplary cochlear lead blank 104b is identical to the cochlear lead 104, but for the absence of windows, and similar elements are represented by similar reference numerals. To that end, the exemplary cochlear lead blank 104b includes an electrode array blank 116b as well as the wing 118. In other implantations, the wing 118 may be omitted and added to a completed electrode array (if so desired). The exemplary electrode array blank 116b has a flexible body 120b and a plurality of electrically conductive contacts 122 (e.g., the sixteen contacts 122 illustrated in FIG. 4) spaced along the flexible body between the tip end 124 and the base end 126. The contacts 122 are located inward of the flexibly body outer surface 128b. There are no windows 130 and, given the lack of windows, the contacts 122 are completely covered by the electrically non-conductive material that forms the flexible body 120b and are not exposed. The windows 130 may be formed in a cochlear lead blank such as blank 104b in, for example, the manner described below with reference to FIGS. 21-25.

One exemplary method of forming a cochlear lead blank, such as the cochlear lead blank 104b illustrated in FIGS. 12-15, or merely the electrode array 116b, may involve the use of the exemplary mold 200 illustrated in FIGS. 16-20. Mold 200 has first and second mold parts 202 and 204. The first and second mold parts 202 and 204 include respective plates 206 and 208 with surfaces 210 and 212 that together define an elongate cavity 214 in the shape of the cochlear lead blank 104b. The second mold part 204 also includes one or more inlets 218 for the injected LSR (or other resilient material) that forms the flexible body 120.

While the second mold part 204 is detached from the first mold part 202, the contacts 122 (with the lead wires attached) may be positioned on the cavity defining surface 210 of the plate 206. For example, the contacts 122 may be placed onto the first mold part 202 in series, beginning with contact 122-16 and ending with contact 112-1. The lead wire 136 associated with each contact 122 will extend over the previously positioned contact to and beyond the base end of the mold (the right end in the orientation illustrated in FIG. 16). The contacts 122 are held in place with a small quantity of resilient material 120' (FIGS. 17 and 18) that will become part of the blank flexible body 120b during the molding process. Suitable resilient material 120' includes, but is not limited to, any of the resilient materials described above that are used to form the flexible body 120.

Figure 17:
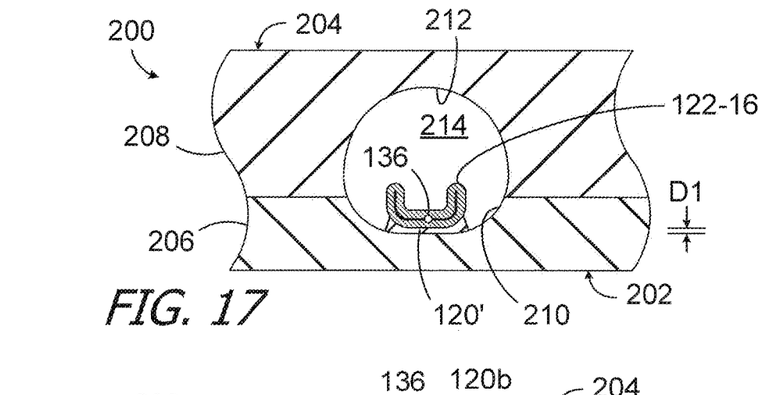
FIG. 17 is a section view of a portion of a method in accordance with one embodiment of a present invention.
Figure 18:
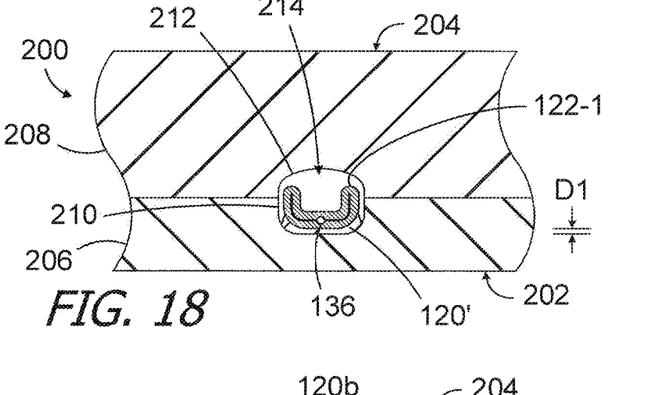
FIG. 18 is a section view of a portion of a method in accordance with one embodiment of a present invention.
Figure 19:
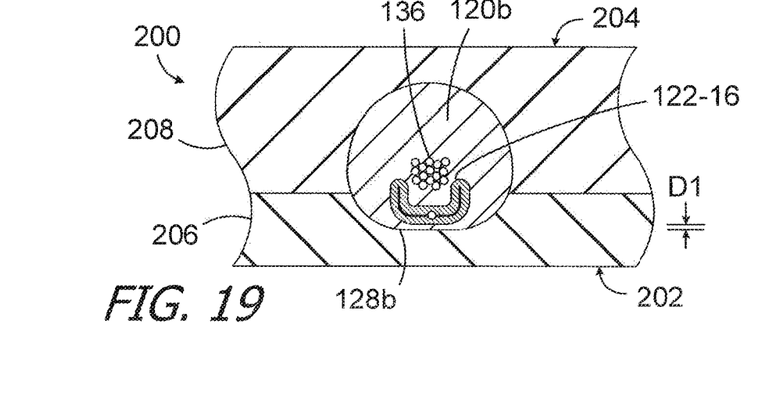
FIG. 19 is a section view of a portion of a method in accordance with one embodiment of a present invention.
Figure 20:
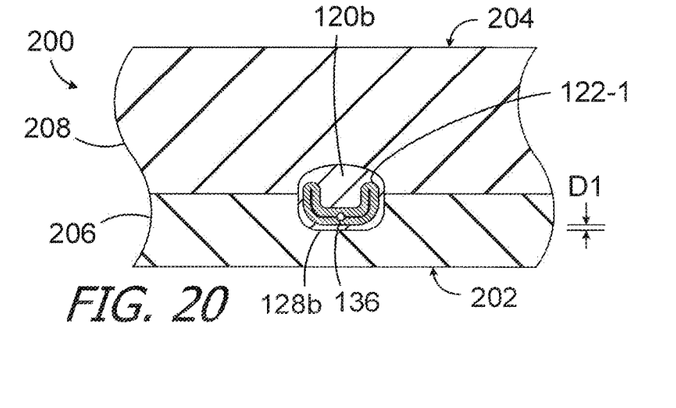
FIG. 20 is a section view of a portion of a method in accordance with one embodiment of a present invention.
Figure 21:
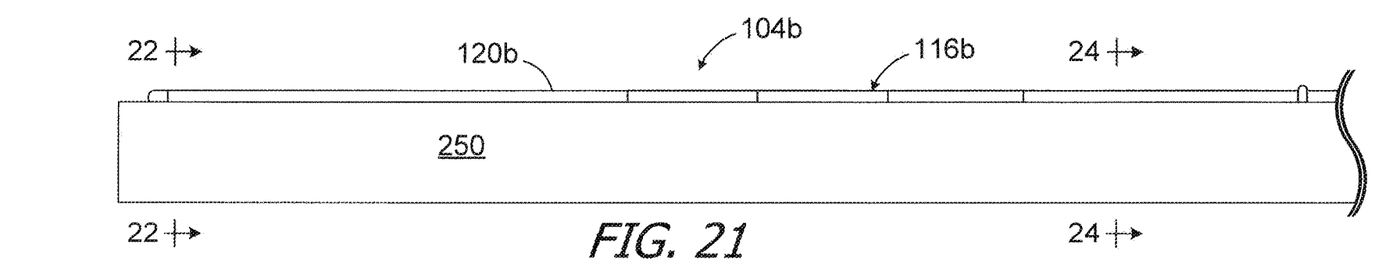
FIG. 21 is a side view of a portion of a method in accordance with one embodiment of a present invention.

Once all of the contacts 122 have been positioned in the first mold part 202, the second mold part 204 may be placed over the first mold part 202 to complete the mold 200 in the manner illustrated in FIGS. 17 and 18. A clamp, screws or other suitable instrumentality (not shown) may be used to hold the mold parts 202 and 204 together. The LSR or other suitable resilient material may then be injected (or otherwise introduced) into the mold cavity 214 to form the flexible body 120. The resilient material 120' separates the contacts from the surface 210 by a distance D1 (FIGS. 17 and 18) in addition to holding the contacts in place 122. As a result, the surfaces of the contacts 122 that are adjacent to the bottom surface of the mold cavity 214 are located inwardly from the exterior surface 128b and the associated portions of the flexible body 120b by the distance D1, and are covered by the flexible body. The remainders of the contacts 122 are also covered by the flexible body 120b due to the differences in size of contacts 122 and the cavity 214 as well as the manner in which the contacts are positioned within the cavity. After the resilient material hardens, the mold parts 202 and 204 may be separated from one another. The completed cochlear lead blank 104b may be removed from the cavity 214.

One exemplary process for forming the windows 130 in the cochlear lead blank 104b to create a cochlear lead 104 is illustrated in FIGS. 21-25. The cochlear lead blank 104b may be placed onto a fixture 250 that is configured to hold the blank in a linear and untwisted state. To that end, the exemplary fixture 250 includes a plate 252, with a groove 254, and a plurality of suction apertures 256. The suction apertures 256 are connected to a source of negative pressure (not shown) by a suction line 258. The suction force holds the cochlear lead blank 104b firmly in place. Portions of the flexibly body 120b corresponding to the windows 130-1 to 130-16 are then removed from the cochlear lead blank 104b, thereby exposing the portions of contacts 122-1 to 122-16, to complete the electrode array 116. In some instances, the cochlear lead blank 104b may be reoriented on a particular fixture, or moved to a different fixture, during the window formation process.

Figure 22:
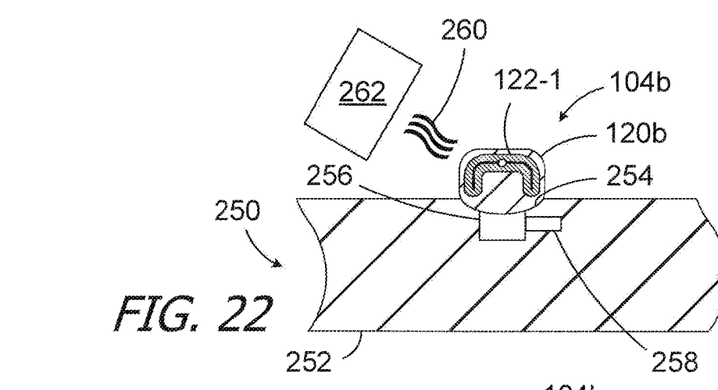
FIG. 22 is a section view of a portion of a method in accordance with one embodiment of a present invention.
Figure 23:
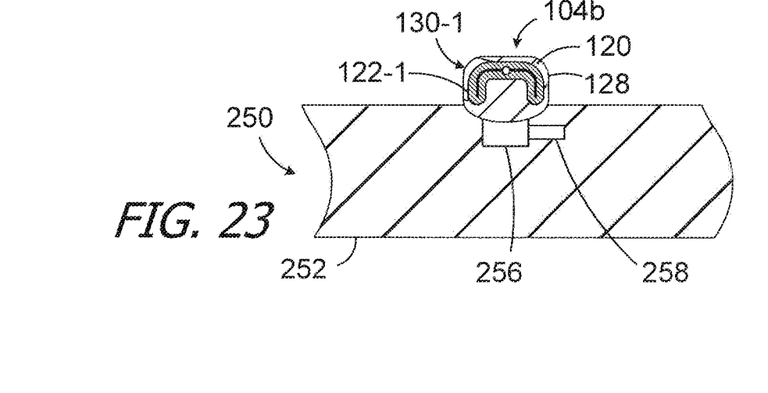
FIG. 23 is a section view of a portion of a method in accordance with one embodiment of a present invention.
Figure 24:
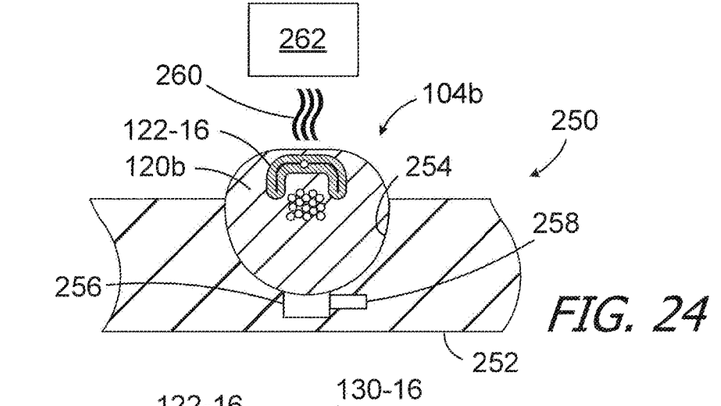
FIG. 24 is a section view of a portion of a method in accordance with one embodiment of a present invention.
Figure 25:
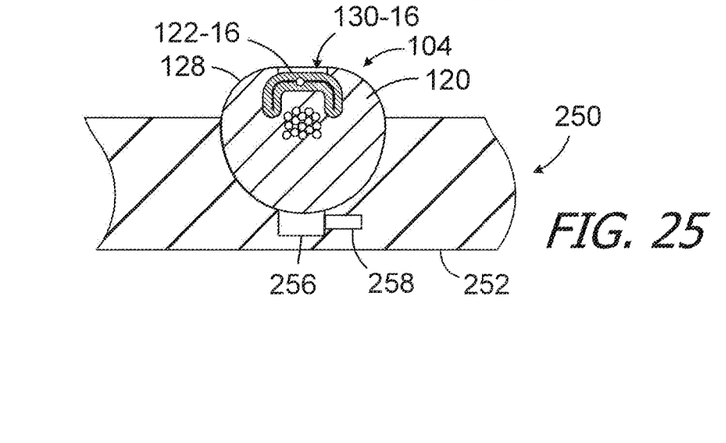
FIG. 25 is a section view of a portion of a method in accordance with one embodiment of a present invention.

Any suitable instrumentality or process may be used to remove material from the cochlear lead blank 104b to form the windows 130 and expose portions of the contacts 122. By way of example, but not limitation, ablation energy 260 (e.g., a laser beam) from an ablation energy source 262 is used to remove material from the cochlear lead blank 104b to form the windows 130 and expose portions of the contacts 122 in the illustrated embodiment. Referring for example to FIGS. 22 and 23, ablation energy 260 may be applied to the cochlear lead blank 104b to form the window 130-1 that is associated with the contact 122-1. Turning to FIGS. 24 and 25, ablation energy 260 may be applied to the cochlear lead blank 104b, and at a location that is parametrically and longitudinally offset from the location illustrated in FIGS. 22 and 23, to form the window 130-16 that is associated with the contact 122-16. The remainder of the windows 130 may be formed in the same way. Other exemplary methods of removing material from a cochlear lead blank include, but are not limited to chemical etching, masking, acid washing, electro-dissolution, electrical discharge machining and mechanical removal (e.g., surface abrasion such as rubbing or grit blasting).

Figure 26:
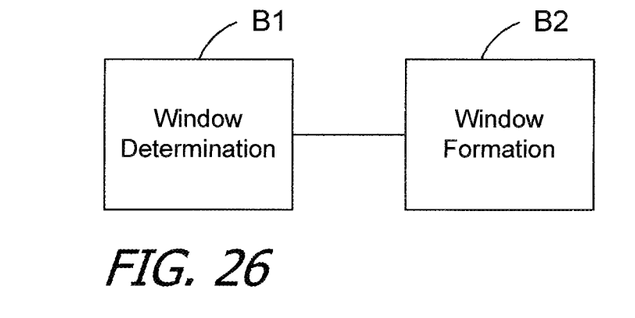
FIG. 26 is a flow chart showing a method in accordance with one embodiment of a present invention.

One exemplary process for producing a cochlear lead from a cochlear lead blank is summarized by the flow chart illustrated in FIG. 26. First, in step B1, the particular features of the contact windows (e.g., parametric orientations and offsets, sizes, spacings, etc.) for the particular cochlear lead are determined. In some instances, the determination is a patient-specific determination that is based on patent-specific data, such as patient scans and/or tonotopic mapping, that can be used to predict rotation of the electrode array within the cochlea (e.g., with physical three-dimensional modeling of the particular patient's scanned cochlea and/or computer simulations of the electrode array insertion into the particular patient's scanned cochlea). The patient-specific scan and/or tonotopic mapping data may also be fed into predictive software, so that the ideal window orientations, offsets, etc. to counteract the predicted effects of rotation can be identified. In those instances where the determinations are not patient-specific, averages based on known cochlea shapes and insertion data may be used. For example, window orientations for a typical left cochlea insertion and window orientations for a typical right cochlea insertion may be determined. Next, in step B2, the windows 130 are formed in a cochlear lead blank, in the manner described above, based on the determined parametric offsets and other window features.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method of forming an electrode array from an electrode array blank, the electrode array blank including a flexible body, defining an exterior surface, a longitudinal axis and a perimeter that extends around the longitudinal axis in planes perpendicular to the longitudinal axis, and a plurality of longitudinally spaced electrically conductive contacts that are below the exterior surface of the flexible body, the method comprising the steps of:
   forming a first window in the flexible body that extends through the exterior of the flexible body to a first one of the electrically conductive contacts, the first window defining a first window perimetric center; and
   forming a second window in the flexible body that extends through the exterior of the flexible body to a second one of the electrically conductive contacts, the second window defining a second window perimetric center that is perimetrically offset from the first window perimetric center when the flexible body is straight and not twisted around the longitudinal axis.

2. A method as claimed in claim 1, further comprising the step of:
   forming a third window in the flexible body that extends through the exterior of the flexible body to a third one of the electrically conductive contacts, the third window defining a third window perimetric center that is perimetrically offset from the first and second window perimetric centers when the flexible body is straight and not twisted around the longitudinal axis.

3. A method as claimed in claim 1, further comprising the step of:
   forming a third window in the flexible body that extends through the exterior of the flexible body to a third one of the electrically conductive contacts, the third window defining a third window perimetric center that is perimetrically aligned with the first window perimetric center when the flexible body is straight and not twisted around the longitudinal axis and is perimetrically offset from the second window perimetric center when the flexible body is straight and not twisted around the longitudinal axis.

4. A method as claimed in claim 1, wherein the steps of forming the first window and forming the second window comprise removing material from the flexible body at longitudinally spaced locations on the flexible body.

5. A method as claimed in claim 1, wherein the step of forming the first and second windows comprises removing material from the flexible body.

6. A method as claimed in claim 5, wherein
removing material from the flexible body comprises laser ablating material from the flexible body.

7. A method as claimed in claim 1, wherein
the electrically conductive contacts have the same shape.

8. A method as claimed in claim 1, wherein
the electrically conductive contacts have different shapes.

9. A method as claimed in claim 1, wherein
the flexible body defines a basal portion having a basal portion stiffness and an apical portion having an apical portion stiffness that is less than the basal portion stiffness.

10. A method as claimed in claim 1, wherein
the flexible body defines a basal portion with a plurality of the electrically conductive contacts and an apical portion with a plurality of the electrically conductive contacts; and
at least one of the electrically conductive contacts in the basal portion extends no more that half-way around the perimeter and at least one of the electrically conductive contacts in the apical portion extends completely around the perimeter.

11. A method as claimed in claim 10, wherein
a plurality of the electrically conductive contacts in the basal portion extends no more that half-way around the perimeter.

12. A method as claimed in claim 1, wherein
the second window is adjacent to, and longitudinally spaced from, the first window with no other window therebetween.

13. A method as claimed in claim 1, wherein
after the first window is formed, the perimeter of the electrode array blank at location longitudinally aligned with the first window is defined solely by the flexible body exterior surface and the first window; and
after the first window is formed, the perimeter of the electrode array blank at location longitudinally aligned with the second window is defined solely by the flexible body exterior surface and the second window.

14. A method as claimed in claim 1, wherein
the first window is formed at a first orientation relative the first one of the electrically conductive contacts; and
the second window is formed at a second orientation, which is different than the first orientation, relative the second one of the electrically conductive contacts.

15. A method of forming an electrode array from an electrode array blank, the electrode array blank including a flexible body, defining an exterior surface, a longitudinal axis and a perimeter that extends around the longitudinal axis in planes perpendicular to the longitudinal axis, and a plurality of longitudinally spaced electrically conductive contacts that are below the exterior surface of the flexible body, the method comprising the steps of:
forming a first window in the flexible body that extends through the exterior of the flexible body to a first one of the electrically conductive contacts, the first window defining a first window perimetric center;
forming a second window in the flexible body that extends through the exterior of the flexible body to a second one of the electrically conductive contacts, the second window defining a second window perimetric center that is perimetrically offset from the first window perimetric center when the flexible body is straight and not twisted around the longitudinal axis; and
prior to forming the first and second windows, determining an amount that the second window perimetric center should be perimetrically offset from the first window perimetric center.

16. A method as claimed in claim 15, wherein
the amount that the second window perimetric center should be perimetrically offset corresponds to an array rotation prediction based on patient-specific data.

17. A method as claimed in claim 16, wherein
the patient-specific data comprises the results of at least one of a patient scan and a tonotopic mapping procedure.

18. A method as claimed in claim 16, wherein
the array rotation prediction is the result of a computer simulation of the insertion of the electrode array into the patient's cochlea.

19. A method as claimed in claim 18, wherein
the amount that the second window perimetric center should be perimetrically offset corresponds to averages based on known cochlea shapes and insertion data.

20. A method, comprising the steps of:
inserting an electrode array into a cochlea having a modiolus, the electrode array including a flexible body, defining an exterior surface, a longitudinal axis and a perimeter that extends around the longitudinal axis in planes perpendicular to the longitudinal axis, a plurality of longitudinally spaced electrically conductive contacts that are below the exterior surface of the flexible body, and a plurality of longitudinally spaced windows that extend through the exterior of the flexible body to a respective electrically conductive contact and that define respective window perimetric centers, the window perimetric centers of at least some of the windows being perimetrically offset from the window perimetric centers of other windows when the flexible body is straight; and
allowing at least a portion of the electrode array to twist a predetermined amount around the longitudinal axis during the insertion such that the window perimetric centers of all of the windows of the electrode array face the modiolus when the electrode array is fully inserted into the cochlea.

21. A method as claimed in claim 20, wherein
the electrode array includes a apical portion and a basal portion;
the window perimetric centers of the window in the apical portion are perimetrically offset from one another.

22. A method as claimed in claim 21, wherein
the window perimetric centers of the window in the basal portion are not perimetrically offset from one another.

* * * * *